(12) United States Patent
Yang et al.

(10) Patent No.: US 6,410,807 B1
(45) Date of Patent: Jun. 25, 2002

(54) SYNTHESIS OF CYCLOHEXENE DIMETHANOL COMPOUNDS

(75) Inventors: Hu Yang, San Ramon; Ta Yen Ching, Novato; Gangfeng Cai, Danville, all of CA (US)

(73) Assignee: Chevron Phillips Chemical Company LP, Houston, TX (US)

( * ) Notice: Subject to any disclaimer, the term of this patent is extended or adjusted under 35 U.S.C. 154(b) by 0 days.

(21) Appl. No.: 09/567,593

(22) Filed: May 10, 2000

(51) Int. Cl.$^7$ ............................................. C07C 31/20
(52) U.S. Cl. ..................................... 568/831; 568/823
(58) Field of Search ................................. 568/823, 831

(56) References Cited

U.S. PATENT DOCUMENTS

| | | | | |
|---|---|---|---|---|
| 2,417,100 A | * | 3/1947 | Bruson | 568/823 |
| 2,999,865 A | * | 9/1961 | Phillips | 568/823 |
| 3,057,815 A | * | 10/1962 | Bartlett | 568/823 |
| 3,110,688 A | * | 11/1963 | Campbell | 568/823 |
| 3,239,539 A | * | 3/1966 | Bartlett | 568/823 |
| 3,278,607 A | * | 10/1966 | Lussling | 568/823 |
| 3,497,571 A | | 2/1970 | Tellier et al. | 260/844 |
| 3,536,687 A | | 10/1970 | Nordstrom | 260/89.5 |
| 4,122,290 A | * | 10/1978 | Immel | 568/823 |
| 4,181,810 A | * | 1/1980 | Immel | 568/823 |
| 4,415,370 A | | 11/1983 | Barnabeo et al. | 525/330.6 |
| 4,524,201 A | | 6/1985 | Barnabeo et al. | 528/395 |
| 4,774,225 A | * | 9/1988 | Giraudo | 568/823 |
| 5,095,153 A | * | 3/1992 | Agnes | 568/823 |
| 5,116,916 A | | 5/1992 | Young | 525/350 |
| 5,211,875 A | | 5/1993 | Speer et al. | 252/188.28 |
| 5,346,644 A | | 9/1994 | Speer et al. | 252/188.28 |
| 5,425,896 A | | 6/1995 | Speer et al. | 252/188.28 |
| 5,466,756 A | | 11/1995 | Roach et al. | 525/330.6 |
| 5,498,364 A | | 3/1996 | Speer et al. | 252/188.28 |
| 5,627,239 A | | 5/1997 | Ching et al. | 525/330.6 |
| 5,641,825 A | | 6/1997 | Bacskai et al. | 524/398 |
| 5,656,692 A | | 8/1997 | Hayes | 525/63 |
| 5,660,761 A | | 8/1997 | Katsumoto et al. | 252/188.28 |
| 5,700,554 A | | 12/1997 | Speer et al. | 428/220 |
| 5,736,616 A | | 4/1998 | Ching et al. | 525/330.3 |
| 5,776,361 A | | 7/1998 | Katsumoto et al. | 252/188.28 |
| 5,837,158 A | | 11/1998 | Shepodd et al. | 252/181.6 |
| 5,859,145 A | | 1/1999 | Ching et al. | 525/330.6 |
| 6,057,013 A | | 5/2000 | Ching et al. | 428/35.7 |
| 6,063,307 A | | 5/2000 | Shepodd et al. | 252/181.6 |
| 6,080,896 A | * | 6/2000 | Ninomiya | 568/823 |

FOREIGN PATENT DOCUMENTS

| | | |
|---|---|---|
| DE | 922 648 | 1/1955 |
| DE | 922648 | * 1/1955 |
| WO | WO99/48963 | 9/1999 |

OTHER PUBLICATIONS

French et al., *J. Am. Chem. Soc.*, pp. 1497–1499 (Jul. 1942).

Bruns et al., *Tetrahedron* 35:2523–2530 (1979).

Ching et al., "Tasteless Oxygen Scavenging Polymers: A New Platform Technology for Food Packaging Based On Controlled Oxidation," *Oxygen Absorber . . . 2001 and Beyond*, OSP Conference, pp. 1–8 (Chicago, Jun. 19–20, 2000).

Ching et al., "Tasteless Oxygen Scavenging Polymers: A New Platform Technology for Food Packaging Based On Controlled Oxidation," *Oxygen Absorber . . . 2001 and Beyond*, OSP Conference Slides (Chicago, Jun. 19–20, 2000).

Bruns et al., "Synthesis and Configurational Assignment of Diastereomeric 2,4–Dioxaspiro[5.5]Undec–8–Enes," *Tetrahedron* 35:2523–2530 (1979).

PCT/US01/10960 Search Report (Oct. 19, 2001).

Shortridge, *J. Am. Chem. Soc.*, vol. 70, pp. 946–949 (1948).*

Whitmore, *J. Am. Chem. Soc.*, vol. 63, pp. 124–127 (1941).*

Ault, "Techniques and Experiments for Organic Chemistry," 4th Ed., pp. 142–146 (1983).*

* cited by examiner

Primary Examiner—Michael L. Shippen
(74) Attorney, Agent, or Firm—Williams, Morgan & Amerson, P.C.

(57) ABSTRACT

A process for producing cyclohexene dimethanol or cyclohexane dimethanol compounds is provided. By controlling the rates of addition of certain reaction components and/or by controlling reaction solution temperatures at specific stages during synthesis, this invention provides a process for producing high purity cyclohexene dimethanol or cyclohexane dimethanol compounds without the need for solvent extraction and/or recrystallization procedures.

34 Claims, No Drawings

SYNTHESIS OF CYCLOHEXENE DIMETHANOL COMPOUNDS

TECHNICAL FIELD OF THE INVENTION

This invention relates generally to methods for synthesizing cyclohexene dimethanol or cyclohexane dimethanol compounds, and, more particularly, to methods for obtaining cyclohexene dimethanol or cyclohexane dimethanol compounds in high yields and having high purity while eliminating certain costly and time-intensive procedures associated with solvent extraction and product recrystallization.

BACKGROUND OF THE INVENTION

Cyclohexene dimethanol compounds, such as 3-cyclohexene-1,1-dimethanol, have been used as monomers for synthesizing high performance active barrier polymers which are currently under intensive development as next generation food and beverage packaging technology. (See, for example, PCT Publication No. WO 99/48963, assigned to Chevron Chemical Co.). A prior synthesis approach for producing such compounds is based on the Cannizzaro reaction. For example, in synthesizing 3-cyclohexene-1,1-dimethanol by this approach, two mole of formaldehyde reacts with one mole of tetrahydrobenzaldehyde in the presence of one mole of base, e.g., sodium hydroxide or potassium hydroxide, in an aqueous alcoholic solution. The reaction presumably follows the course indicated by the following:

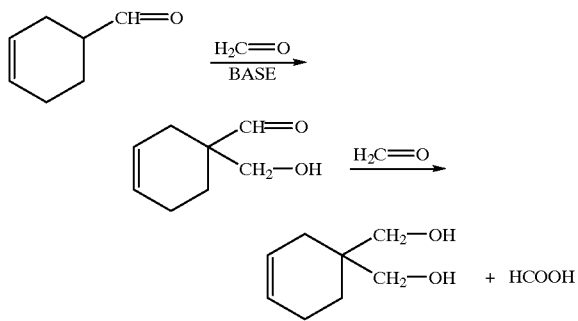

This process has typically involved a reaction stage in aqueous or aqueous-alcoholic medium, followed by a purification stage that requires multiple extraction steps with organic solvent, a distillation step and a recrystallization step from a suitable organic solvent. In one example (H. E. French and D. M. Gallagher, JACS 1942, p 1497), a reaction was conducted in an aqueous-alcoholic medium in the presence of potassium hydroxide at 70° C. The purification stage involved the extraction of the reaction medium with ether, followed by distillation to remove the solvent. The crude product was an oil residue that solidified upon standing over time. Recrystallization of the product gave a yield reported to be in the range of 50–60%. The melting point, which served as an indication of product purity, was reported to be 92.5° C.

In a separate report (Klaus Bruns and Jens Conard, *Tetrahydron*, Vol. 35, p2523, 1979), a reaction stage was carried out in aqueous sodium hydroxide, while the purification stage involved multiple extractions with methylisobutylketone, a specialty solvent. The crude yield, reported to be 92%, was based on the residue from the evaporation of the solvent, and no further purification was described. We performed this procedure and found that it does not provide a level of purity sufficient for making polymerization grade 3-cyclohexene-1,1-dimethanol. Moreover, further purification steps necessary to achieve a sufficient level of purity led to unacceptably low yields.

When considering the commercial scale production of 3-cyclohexene-1,1-dimethanol and other cyclohexene dimethanol or cyclohexane dimethanol compounds, the involvement of large quantities of expensive organic solvents and long cycle times for multiple organic/aqueous extractions and crystallizations make the prior processes undesirable from both a material and operational cost standpoint. Indeed, the number of operation units, such as organic solvent storage tanks, mixing tanks and distillation units contribute significantly to the overall cost of producing these compounds. In light of this, significant benefits could be realized by eliminating one or more of the operational steps associated with product extraction and/or recrystallization.

The present invention overcomes, or at least reduces the effects of, one or more of the aforementioned problems.

SUMMARY OF THE INVENTION

According to a first aspect of the present invention, a method is provided for producing a cyclohexene dimethanol or a cyclohexane dimethanol compound, comprising:

(a) adding a base solution to a formaldehyde solution to form a formaldehyde/base solution;

(b) adding an aldehyde to the formaldehyde/base solution to form a reaction solution; and (c) recovering cyclohexene dimethanol or cyclohexane dimethanol product from said reaction solution.

According to another aspect of the invention, a method is provided for producing a cyclohexene dimethanol or a cyclohexane dimethanol compound, comprising:

(a) adding a base solution to a formaldehyde solution to form a formaldehyde/base solution;

(b) adding an aldehyde to the formaldehyde/base solution to form a reaction solution;

(c) heating the reaction solution to a temperature about 70° C. or less;

(d) cooling the reaction vessel contents to between about 10° C. and 30C; and (e) recovering cyclohexene dimethanol or cyclohexane dimethanol product from said reaction solution.

According to another aspect of the invention, a method is provided for producing 3-cyclohexene-1,1-dimethanol having a yield greater than about 80% and a purity greater than about 95%, comprising:

(a) adding a base solution to a formaldehyde solution to form a formaldehyde/base solution, wherein the temperature of the formaldehyde/base solution is maintained between about 10° C. and about 20° C. during addition of said base solution;

(b) adding a tetrahydrobenzaldehyde, to the formaldehyde/base solution to form a reaction solution, wherein the temperature of the reaction solution is maintained between about 10° C. and about 20° C. during addition of said tetrahydrobenzaldehyde;

(c) maintaining the temperature of the reaction solution between about 15° C. and about 25° C. for at least about 4 hours following addition of said tetrahydrobenzaldehyde;

(d) heating the reaction solution to a temperature between about 50° C. and about 60° C. for at least about 0.5 hours to about 2 hours;

(e) cooling the reaction vessel contents to between about 10° C. and about 30° C.; and (f) recovering crystalline-form 3-cyclohexene-1,1-dimethanol product from said reaction solution.

DETAILED DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

In order to develop an economically viable process for making cyclohexene dimethanol or cyclohexane dimethanol compounds, we have investigated alternative processes effective for eliminating organic solvent-based extraction and/or recrystallization steps during the purification stage of the process. In addition, we also sought to further improve product yield while- maintaining sufficient product purity.

According to the present invention, high purity cyclohexene dimethanol or cyclohexane dimethanol can be obtained in a crystalline form by controlling certain process parameters during the progress of the synthesis reaction. In particular, we have found that by controlling the rate of addition of certain reagents and the temperature profile during the reaction stage, cyclohexene dimethanols or cyclohexane dimethanols can be produced having high purity while eliminating some or all of the steps of solvent extraction and/or recrystallization required by prior synthesis methods. In contrast to prior methods, the present invention provides high purity crystalline-form product that can be obtained directly from the reaction medium.

According to the present invention, a cyclohexene dimethanol or a cyclohexane dimethanol is synthesized by reacting formaldehyde with an aldehyde, preferably an aldehyde with from 2 to about 20 carbon atoms, more preferably tetrahydrobenzaldehyde or cyclohexane carboxyaldehyde, in the presence of base in an aqueous or aqueous-alcoholic solution. The reaction vessel employed, e.g., a 4-neck flask or the like, is not critical. The reaction vessel can be suitably equipped with a mechanical stirrer or some other means for effecting agitation of the reaction medium, a thermometer, a nitrogen circulation, an external cooling source, such as a cooling bath, and/or any other feature necessary or desired for a given application.

The process is typically performed by first charging a reaction vessel with formaldehyde. To this formaldehyde solution, a base solution is added, preferably under some form of agitation. The base will typically be an aqueous base solution, for example a sodium hydroxide or potassium hydroxide solution. The base solution can also comprise an aqueous-alcoholic solution, if desired, comprising an alcohol such as propanol, ethanol, butanol or the like, in addition to an aqueous component. Theoretically, the amount of base required to be added to the formaldehyde to ensure substantial completion of the synthesis reaction that will follow is 1 equivalent of base to 2 equivalents of formaldehyde. Of course, for practical reasons, the relative amounts of these and other components of the reaction may be varied depending on the particular implementation of the invention.

Under basic conditions, formaldehyde can undergo a polymerization reaction that is undesirable in the context of this synthesis reaction since it represents a source for contaminating by-products that can degrade both the yield and purity of the desired product. Therefore, it is preferred that during the addition of the base solution to the formaldehyde solution, the temperature of the reaction vessel contents are maintained sufficiently low so as to minimize formaldehyde polymerization. This can most readily be achieved by controlling the temperature of the reaction vessel contents, for example using a suitable cooling source such as a cooling bath or another cooling means available in the art. Moreover, the rate of addition of the base solution to the formaldehyde solution can contribute to this formaldehyde polymerization by increasing the temperature of the reaction solution. Thus, in addition to the use of an external cooling source, the rate of addition of the base solution to the formaldehyde solution is preferably controlled as well.

Therefore, in certain illustrative embodiments of the present invention, an external cooling source is used to maintain the temperature of the reaction vessel contents between about 5° C. and about 40° C., more preferably between about 10° C. and about 30° C., and most preferably between about 10° C. and about 20° C., during the addition of the base solution to the formaldehyde solution, and the rate of addition of the base solution to the formaldehyde solution is controlled such that the temperature of the reaction vessel contents throughout this addition is maintained within these desired temperature ranges.

After the base solution has been added, an aldehyde is introduced into the reaction vessel, preferably under some form of agitation. In one preferred embodiment of the invention, the aldehyde is a tetrahydrobenzaldehyde, more preferably 1,2,5,6-tetrahydrobenzaldehyde, used in a reaction for producing 3-cyclohexene-1,1-dimethanol. It will be recognized by the skilled artisan that many structural features of the tetrahydrobenzaldehyde starting material can be varied, and that this will dictate the structural features of the cyclohexene dimethanol produced therefrom. Thus, if it is desired to produce a cyclohexene dimethanol containing, for example, substitutions at some point along the cyclohexene ring of the product molecule, this can be achieved by selecting the correspondingly substituted tetrahydrobenzaldehyde starting material for use in the reaction.

Alternatively, the aldehyde can be a cyclohexane carboxyaldehyde and can be used in a reaction for producing cyclohexane-1,1-dimethanol. Again, it will be recognized by the skilled artisan that many structural features of the cyclohexane carboxyaldehyde starting material can be varied, and that this will dictate the structural features of the cyclohexane dimethanol produced therefrom. Thus, if it is desired to produce a cyclohexane dimethanol containing, for example, substitutions at some point along the cyclohexane ring of the product molecule, this can be achieved by selecting the correspondingly substituted cyclohexane carboxyaldehyde starting material for use in the reaction.

In a theoretical sense, 1 equivalent of aldehyde is added for every 2 equivalents of formaldehyde that was added previously to the reaction vessel. However, as will be recognized by the skilled artisan, these are not absolute limitations on the practice of this invention. Rather, the precise amounts of the components used in the synthesis procedure described herein can be varied, as desired, to best suit the needs of a given implementation of this process.

As during the base addition step discussed above, temperature control has been found to be important during addition of the aldehyde to the reaction solution. This temperature control is particularly important in allowing effective crystallization of high purity product directly from the reaction solution. Therefore, an external cooling source is preferably used to maintain the temperature of the reaction vessel contents between about 5° C. and about 40° C., more preferably. between about 10° C. and about 30° C., and most preferably between about 10° C. and about 20° C., during addition of the aldehyde to the formaldehyde/base solution. Moreover, the rate of addition of the aldehyde to the formaldehyde/base solution is preferably controlled such that the temperature of the reaction vessel contents throughout this addition is maintained within these desired temperature ranges.

During the addition of aldehyde under these conditions, some crystalline product develops after an initial emulsion stage. Agitation is preferably maintained during this addition to ensure a largely aggregate-free suspension of crystalline product in the reaction medium. This crystalline product may be recovered, as desired, at this or any stage hereafter.

However, it may be preferred that after addition of the aldehyde is complete, the temperature of the reaction vessel contents is maintained between about 10° C. and about 30° C., preferably between about 15° C. and about 25° C., until the reaction exotherm is dissipated. Illustratively, the reaction vessel contents are maintained at such temperatures for about 1–2 hours, preferably for about 3–4 hours, or more.

At a point after addition of the aldehyde is complete and/or after the reaction vessel contents have been maintained at a temperature between about 10° C. and about 30° C., preferably between about 15° C. and about 25° C., until the reaction exotherm has largely dissipated, the reaction vessel contents can be heated to a temperature up to about 70° C., preferably between about 40° C. and about 70° C., more preferably between about 50° C. and about 60° C., for several minutes to several hours, in order to facilitate the reaction of any unreacted formaldehyde and aldehyde. Higher temperatures allow the reaction to proceed more rapidly, but temperatures greater than about 70° C. lead to unacceptably high levels of side products.

Subsequent to this heating, the reaction vessel contents are then allowed to cool, typically to a temperature in the range of about 15° C. to about 25° C., in order to effect crystallization of product remaining in solution. Preferably, this cooling is performed under some form of agitation in order to prevent aggregation of the crystalline product.

By practice of the disclosed invention, a high-purity crystalline product can be obtained. The crystalline product can be recovered from the reaction solution by any of a variety of techniques known in the art, e.g., by suction filtration, centrifugation, etc. The material that is collected by filtration will typically in the form of a wet-cake that is then dried to obtain solid, crystalline product. If desired, one or more rinses of the wet-cake with water or an aqueous-based solution can be used to help remove any impurities that may have remained in the crystalline product. For example, these rinses can involve first immersing the wet-cake in water without vacuum and allowing it to sit for several minutes or hours before vacuum is applied to remove the rinse solution.

The wet-cake can be left at ambient temperature to dry or can be dried at an elevated temperature, for example in a vacuum oven, a tumble dryer, or the like. The wet-cake can be dried at essentially any elevated temperature provided it does not exceed the melting temperature of the cyclohexene dimethanol or cyclohexane dimethanol product. Of course, it will be understood that the drying time necessary to dry the wet-cake will be inversely related to the drying temperature employed, and, thus, these conditions can be varied as a matter of operational convenience.

The purity of the product obtainable by this process is typically greater than 85%, preferably greater than about 95%, more preferably greater than about 99%. The high purity of the cyclohexene dimethanol product obtainable by practice of the present invention was confirmed by both melting point (m.p.>92–93° C.) and GC analysis (>99%).

The yield of the product is generally greater than about 70%, more preferably greater than about 80%. In addition, yield can be further improved if product remaining in the filtrate is extracted with a suitable organic solvent. In this way, an additional quantity of product can be recovered. Since this can be done on an accumulative basis from lot to lot, and the quantity of organic solvent used is very small, and recyclable, this will further improve the economy of the process.

Thus, in another embodiment, the quantity of product remaining in the filtrate is solvent extracted, for example with methylisobutylketone, or another suitable organic solvent. The organic phase can be condensed and the solid obtained therefrom is recrystallized, for example from acetone or ethanol, to yield additional pure product. Total product yields of 85% or more can be achieved according to this embodiment of the invention.

The following examples are provided to demonstrate certain illustrative embodiments of this invention. It should be appreciated by those skilled in the art that the techniques disclosed in the examples which follow represent those found by the inventors to function in the practice of the invention and thus can be considered to constitute examples of illustrative modes for its practice. However, those skilled in the art should, in light of the present disclosure, appreciate that many changes can be made in the specific embodiments which are disclosed and still obtain a like or similar result without departing from the spirit and scope of the invention.

EXAMPLES

Example 1

Synthesis of 3-Cyclohexene-1,1-Dimethanol

A 4-neck flask, equipped with mechanical stirrer, thermometer, a nitrogen circulation, an external cooling bath and an addition funnel, was charged with 184.36 parts of formaldehyde (37 wt. %).

To this solution was added 218.06 parts of sodium hydroxide solution (25 wt. %) by slow addition with an external cooling bath. The addition rate of the sodium hydroxide was controlled such that the content temperature did not exceed 20° C. throughout the addition. During this addition, the temperature was typically maintained between about 10° C. and 20° C.

After addition of the sodium hydroxide, 100 parts 1,2,5,6-tetrahydrobenzaldehyde was introduced through an additional funnel. The rate of addition of the 1,2,5,6-tetrahydrobenzaldehyde was controlled such that the reaction temperature did not exceed 20° C. throughout the addition. During this addition, the temperature was typically maintained between about 10° C. and 20° C. The crystalline form product developed after an initial emulsion stage. An efficient agitation of the contents of the flask was found to be important for achieving adequate suspension of the product in the reaction medium. After the addition was complete, the reaction temperature was maintained between 15° C. and 25° C. until the reaction exotherm dissipated. This was followed by heating the reaction content to 55° C. for about one hour. The reaction content was then allowed to cool to room temperature under agitation sufficient to prevent the aggregation of the product.

A white crystalline product was collected by suction filtration from the reaction medium. The wet-cake so collected was washed in a funnel with water. The wet-cake was first immersed in water, without vacuum, and allowed to sit for a few minutes. Vacuum was then applied to drain the water. The product was dried in a vacuum oven at room temperature for about 24 hrs or at elevated temperature for a shorter period of time. The final product was an off-white crystalline material. The yield of the material was 80%. The melting point of the material was 92–93° C.

The small quantity of product that remained in the filtrate was extracted with small amount of methylisobutylketone. The organic phase was condensed and the white solid that was obtained was recrystallized from acetone or ethanol to yield additional pure product. This resulted in a total yield of 85%.

The particular embodiments disclosed above are illustrative only, as the invention may be modified and practiced in different but equivalent manners apparent to those skilled in the art having the benefit of the teachings herein. More specifically, it will be apparent that certain agents which are chemically related may be substituted for the agents described herein while the same or similar results would be achieved. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed:

1. A method for producing a cyclohexene dimethanol or a cyclohexane dimethanol compound, comprising:
    (a) adding a base solution to a formaldehyde solution to form a formaldehyde/base solution;
    (b) adding an aldehyde selected from the group consisting of tetrahydrobenzaldehydes and cyclohexane carboxyaldehyde to the formaldehyde/base solution to form a reaction solution;
    (c) maintaining the temperature of the reaction solution between about 10° C. and about 30° C. for at least about 1 hr; and
    (d) recovering cyclohexene dimethanol or cyclohexane dimethanol product from said reaction solution.

2. The method of claim 1, wherein the temperature of the formaldehyde/base solution is maintained between about 5° C. and about 30° C. during addition of said base solution; and wherein the temperature of the reaction solution is maintained at a temperature between about 5° C. and about 30° C. during addition of said aldehyde.

3. The method of claim 2, wherein the temperature of the formaldehyde/base solution is maintained between about 10° C. and about 20° C. during addition of said base solution.

4. The method of claim 2, wherein the temperature of the reaction solution is maintained at a temperature between about 10° C. and about 20° C. during addition of said aldehyde.

5. The method of claim 1, wherein the aldehyde is a tetrahydrobenzaldehyde.

6. The method of claim 5, wherein the tetrahydrobenzaldehyde is 1,2,5,6-tetrahydrobenzaldehyde.

7. The method of claim 1, wherein the cyclohexene dimethanol product is 3-cyclohexene-1,1-dimethanol.

8. The method of claim 1, wherein the aldehyde is cyclohexane carboxyaldehyde.

9. The method of claim 1, wherein the cyclohexane dimethanol product is cyclohexane-1,1-dimethanol.

10. The method of claim 1, wherein steps (a) and (b) are performed under agitation.

11. The method of claim 1, wherein recovering cyclohexene dimethanol or cyclohexane dimethanol product from said reaction solution comprises at least one filtration or centrifugation step.

12. The method of claim 1, further comprising a drying step after said recovering step.

13. The method of claim 12, wherein said drying step is performed in an oven or tumble dryer.

14. A method for producing a cyclohexene dimethanol or a cyclohexane dimethanol compound, comprising:
    (a) adding a base solution to a formaldehyde solution to form a formaldehyde/base solution;
    (b) adding an aldehyde selected from the group consisting of tetrahydrobenzaldehydes and cyclohexane carboxyaldehyde to the formaldehyde/base solution to form a reaction solution;
    (c) maintaining the temperature of the reaction solution between about 10° C. and about 30° C. for at least about 1 hr;
    (d) heating the reaction solution to a temperature about 70° C. or less;
    (e) cooling the reaction vessel contents to between about 10° C. and 30° C.; and
    (f) recovering cyclohexene dimethanol or cyclohexane dimethanol product from said reaction solution.

15. The method of claim 14, wherein the temperature of the formaldehyde/base solution is maintained between about 5° C. and about 30° C. during addition of said base solution.

16. The method of claim 15, wherein the temperature of the formaldehyde/base solution is maintained between about 10° C. and about 20° C. during addition of said base solution.

17. The method of claim 14, wherein the temperature of the reaction solution is maintained between about 5° C. and about 30° C. during addition of said aldehyde.

18. The method of claim 14, wherein the temperature of the reaction solution is maintained at a temperature between about 10° C. and about 20° C. during addition of said aldehyde.

19. The method of claim 14, wherein step (c) comprises heating the reaction solution to a temperature of at least about 40° C. for at least about 0.5 hours to about 5 hours.

20. The method of claim 19, wherein step (c) comprises heating the reaction solution to a temperature between about 50° C. and 60° C.

21. The method of claim 14, wherein the aldehyde is a tetrahydrobenzaldehyde.

22. The method of claim 21, wherein the tetrahydrobenzaldehyde is 1,2,5,6-tetrahydrobenzaldehyde.

23. The method of claim 14, wherein the cyclohexene dimethanol product is 3-cyclohexene-1,1-dimethanol.

24. The method of claim 14, wherein the aldehyde is cyclohexane carboxyaldehyde.

25. The method of claim 14, wherein the cyclohexane dimethanol product is cyclohexane-1,1-dimethanol.

26. The method of claim 14, wherein steps (a)–(d) are performed under agitation.

27. The method of claim 14, wherein recovering cyclohexene dimethanol or cyclohexane dimethanol product from said reaction solution comprises at least one filtration or centrifugation step.

28. The method of claim 14, further comprising a drying step after said recovering step.

29. The method of claim 28, wherein said drying step is performed in an oven or tumble dryer.

30. A method for producing 3-cyclohexene-1,1-dimethanol having a yield greater than about 80% and a purity greater than about 95%, comprising:

(a) adding a base solution to a formaldehyde solution to form a formaldehyde/base solution, wherein the temperature of the formaldehyde/base solution is maintained between about 10° C. and about 20° C. during addition of said base solution;

(b) adding a tetrahydrobenzaldehyde to the formaldehyde/base solution to form a reaction solution, wherein the temperature of the reaction solution is maintained between about 10° C. and about 20° C. during addition of said tetrahydrobenzaldehyde;

(c) maintaining the temperature of the reaction solution between about 15° C. and about 25° C. for at least about 4 hours following addition of said tetrahydrobenzaldehyde;

(d) heating the reaction solution to a temperature between about 50° C. and about 60° C. for at least about 0.5 hours to about 2 hours;

(e) cooling the reaction vessel contents to between about 10° C. and about 30° C.; and (f) recovering crystalline-form 3-cyclohexene-1,1-dimethanol product from said reaction solution.

31. The method of claim 30, wherein recovering cyclohexene dimethanol product from said reaction solution comprises at least one filtration or centrifugation step.

32. The method of claim 30, further comprising a drying step after said recovering step.

33. The method of claim 32, wherein said drying step is performed in an oven or tumble dryer.

34. The method of claim 30, wherein steps (a)–(d) are performed under agitation.

* * * * *